United States Patent
Muthuswamy (10) Patent No.: US 11,771,368 B2
(45) Date of Patent: Oct. 3, 2023

(54) RAPID ASSESSMENT OF MICROCIRCULATION IN PATIENTS TO REALIZE CLOSED-LOOP SYSTEMS

(71) Applicant: Jitendran Muthuswamy, Chandler, AZ (US)

(72) Inventor: Jitendran Muthuswamy, Chandler, AZ (US)

(73) Assignee: Arizona Board of Regents on behalf of Arizona State University, Scottsdale, AZ (US)

( * ) Notice: Subject to any disclaimer, the term of this patent is extended or adjusted under 35 U.S.C. 154(b) by 173 days.

(21) Appl. No.: 17/196,306

(22) Filed: Mar. 9, 2021

(65) Prior Publication Data

US 2021/0275091 A1 Sep. 9, 2021

Related U.S. Application Data (60) Provisional application No. 62/987,096, filed on Mar. 9, 2020.

(51) Int. Cl.
*A61B 5/02* (2006.01)
*A61B 5/00* (2006.01)
(Continued)

(52) U.S. Cl.
CPC .......... *A61B 5/4836* (2013.01); *A61B 5/0265* (2013.01); *A61B 5/7257* (2013.01);
(Continued)

(58) Field of Classification Search
None
See application file for complete search history.

(56) References Cited

U.S. PATENT DOCUMENTS

| 6,427,079 B1 | 7/2002 | Schneider et al. |
| 8,653,642 B2 | 2/2014 | Sutanto et al. |
| (Continued) | | |

FOREIGN PATENT DOCUMENTS

| AU | 2013201221 A1 | 3/2013 |
| JP | 5978395 B2 | 8/2016 |
| WO | 2020160455 A1 | 8/2020 |

OTHER PUBLICATIONS

Christophersen et al., "Rapid Impedance Spectrum Measurements for State-of-Health Assessment of EnergyStorage Devices," SAE International Journal of Passenger Cars—Electronic and Electrical Systems, vol. 5, No. 1, Apr. 16, 2012, pp. 246-256.

(Continued)

*Primary Examiner* — Ankit D Tejani
(74) *Attorney, Agent, or Firm* — Withrow & Terranova, P.L.L.C.; Vincent K. Gustafson (57) ABSTRACT

Rapid assessment of microcirculation in tissue to realize closed-loop systems is provided. Microcirculatory assessment systems according to embodiments described herein allow a user to assess changes in local blood flow in microvasculature in real-time using conventional electrical techniques. Some embodiments provide a closed-loop system that allows calibrated doses of electrical stimulation to be delivered in a deep brain stimulation (DBS) system depending on blood flow changes (in specific regions of the brain) being fed back to a controller. The approach described here is readily translatable with very minimal changes to existing hardware. Such closed-loop systems will improve the accuracy of electrode placement in DBS surgery and potentially reduce surgery time, optimize the delivery of electrical stimulation, increase battery life of implantable DBS systems, reduce post-surgical visits to medical practitioners and improve the quality of life of patients.

19 Claims, 10 Drawing Sheets

(51) Int. Cl.
*A61B 5/0265* (2006.01)
*A61N 1/36* (2006.01)
*A61N 1/05* (2006.01)

(52) U.S. Cl.
CPC ....... *A61N 1/0534* (2013.01); *A61N 1/36135* (2013.01); *A61B 5/4839* (2013.01)

(56) References Cited

U.S. PATENT DOCUMENTS

| | | | |
|---|---|---|---|
| 9,067,272 | B2 | 6/2015 | Sutanto et al. |
| 10,589,124 | B2 | 3/2020 | Smith et al. |
| 10,835,184 | B2 | 11/2020 | Muthuswamy et al. |
| 10,974,065 | B2 | 4/2021 | Smith et al. |
| 2005/0173267 | A1 | 8/2005 | Muthuswamy et al. |
| 2006/0025841 | A1* | 2/2006 | McIntyre ............ A61N 1/0534 607/116 |
| 2018/0348140 | A1 | 12/2018 | Quint et al. |
| 2019/0030230 | A1* | 1/2019 | Connor ............... A61M 60/148 |
| 2019/0183392 | A1* | 6/2019 | Hsiai ................. G01N 29/00 |
| 2019/0247668 | A1 | 8/2019 | Towe et al. |
| 2020/0245910 | A1 | 8/2020 | Mallas et al. |
| 2021/0023362 | A1 | 1/2021 | Lorenzo et al. |
| 2021/0121129 | A1 | 4/2021 | Muthuswamy et al. |

OTHER PUBLICATIONS

Wardell et al., "Relationship Between Laser Doppler Signals and Anatomy During Deep Brain Stimulation Electrode Implantation Toward the Ventral Intermediate Nucleus and Subthalamic Nucleus," Operative Neurosurgery 2, vol. 72, Nov. 27, 2012, 14 pages.
Xu et al., "Measuring Electrolyte Impedance and Noise Simultaneously by TriangularWaveform Voltage and Principal Component Analysis." Sensors, MDPI, vol. 16, No. 4:576, 15 pages.
Muthuswamy, J., U.S. Appl. No. 17/196,324, filed Mar. 9, 2021.
Smith et al., U.S. Appl. No. 17/225,711, filed Apr. 8, 2021.
Sridharan et al., U.S. Appl. No. 16/322,759, filed Feb. 1, 2019.
Rakoze et al., U.S. Appl. No. 17/113,638, filed Dec. 7, 2020.
Non-Final Office Action for U.S. Appl. No. 17/196,324, dated Jul. 13, 2022, 24 pages.
Final Office Action for U.S. Appl. No. 17/196,324, dated Feb. 15, 2023, 17 pages.
Non-Final Office Action for U.S. Appl. No. 17/196,324, dated Jun. 6, 2023, 20 pages.

* cited by examiner

RAPID ASSESSMENT OF MICROCIRCULATION IN PATIENTS TO REALIZE CLOSED-LOOP SYSTEMS

RELATED APPLICATIONS

This application claims the benefit of provisional patent application Ser. No. 62/987,096, filed Mar. 9, 2020, the disclosure of which is hereby incorporated herein by reference in its entirety.

The present application is related to concurrently filed U.S. patent application Ser. No. 17/196,324 filed on Mar. 9, 2021 (subsequently published as U.S. Patent Application Publication No. 2021/0278450 A1), entitled "Systems and Methods to Determine Electrochemical Impedance Spectrogram Rapidly in Real Time," the disclosure of which is hereby incorporated herein by reference in its entirety.

GOVERNMENT SUPPORT

This invention was made with government support under 1650566 awarded by the National Science Foundation. The government has certain rights in the invention.

FIELD OF THE DISCLOSURE

This disclosure relates to monitoring blood flow in tissue of patients, such as with medical devices and/or during medical procedures.

BACKGROUND

Assessments of blood flow in the cerebral microvasculature and vasculature in other parts of the body are critical during surgery, and particularly in neurosurgery. However, conventional non-invasive measurements of blood flow monitoring such as Xe-CT, MRI, and PET involve transportation of patients and/or cumbersome instrumentation that provide "snap-shots" of local blood flow information. Laser Doppler perfusion measurements provide an optical method to assess local blood flow in the immediate vicinity (~1 cubic millimeter ($mm^3$) volume around the tip) of invasive optical fibers that could be implanted in brain and other tissues that are undergoing surgery.

Blood flow in the microvasculature is indicative of a variety of clinically important biomarkers such as presence of local hemorrhage, progression and restoration of injury, neuronal activity, etc. Changes in blood flow in response to focal stimulation of a specific brain region (such as subthalamic nuclei (STN) or ventral intermediate nucleus (VIM) for mitigation of tremor in Parkinsonian patients) indicates the activation of direct and indirect neuronal pathways that can be as far as several centimeters away from the site of stimulation. In the specific case of deep brain stimulation (DBS) of the STN and VIM, consistent changes in blood flow have been observed both in rodents and Parkinsonian patients in cortical and other regions of the brain.

SUMMARY

Rapid assessment of microcirculation in tissue to realize closed-loop systems is provided. Microcirculatory assessment systems according to embodiments described herein allow a user to assess changes in local blood flow in microvasculature in real-time using conventional electrical techniques. The approach described herein can be used to assess hemorrhage during surgery, monitor progress and restoration after injury, monitor neuronal responses to stimulation of specific brain regions, etc. Some embodiments provide a closed-loop system that allows controlled administration of a therapeutic intervention to be delivered depending on blood flow changes being fed back to a controller. For example, calibrated doses of electrical stimulation can be delivered in a deep brain stimulation (DBS) system.

The approach described here is readily translatable with very minimal changes to existing hardware. Such closed-loop systems will improve the accuracy of therapeutic interventions, such as to improve electrode placement in DBS surgery and potentially reduce surgery time, optimize the delivery of therapeutic dosage (e.g., a dosage of electrical stimulation), increase battery life of implantable medical devices (e.g., DBS systems), reduce post-surgical visits to medical practitioners, and improve the quality of life of patients.

An exemplary embodiment provides a method for providing a controlled therapeutic intervention. The method includes applying a therapeutic intervention to a patient; measuring a change in local blood flow in the patient in response to the therapeutic intervention; and adjusting the therapeutic intervention based on the change in local blood flow.

Another exemplary embodiment provides a therapeutic intervention system. The therapeutic intervention system includes an intervention controller configured to provide a controlled therapeutic intervention to a patient; and a microcirculatory assessment system configured to measure a change in local blood flow in the patient in response to the controlled therapeutic intervention. The intervention controller is further configured to adjust the controlled therapeutic intervention based on the change in local blood flow.

Those skilled in the art will appreciate the scope of the present disclosure and realize additional aspects thereof after reading the following detailed description of the preferred embodiments in association with the accompanying drawing figures.

BRIEF DESCRIPTION OF THE DRAWING FIGURES

The accompanying drawing figures incorporated in and forming a part of this specification illustrate several aspects of the disclosure, and together with the description serve to explain the principles of the disclosure.

DETAILED DESCRIPTION

The embodiments set forth below represent the necessary information to enable those skilled in the art to practice the embodiments and illustrate the best mode of practicing the embodiments. Upon reading the following description in light of the accompanying drawing figures, those skilled in the art will understand the concepts of the disclosure and will recognize applications of these concepts not particularly addressed herein. It should be understood that these concepts and applications fall within the scope of the disclosure and the accompanying claims.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of the present disclosure. As used herein, the term "and/or" includes any and all combinations of one or more of the associated listed items.

It will be understood that when an element such as a layer, region, or substrate is referred to as being "on" or extending "onto" another element, it can be directly on or extend directly onto the other element or intervening elements may also be present. In contrast, when an element is referred to as being "directly on" or extending "directly onto" another element, there are no intervening elements present. Likewise, it will be understood that when an element such as a layer, region, or substrate is referred to as being "over" or extending "over" another element, it can be directly over or extend directly over the other element or intervening elements may also be present. In contrast, when an element is referred to as being "directly over" or extending "directly over" another element, there are no intervening elements present. It will also be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

Relative terms such as "below" or "above" or "upper" or "lower" or "horizontal" or "vertical" may be used herein to describe a relationship of one element, layer, or region to another element, layer, or region as illustrated in the Figures. It will be understood that these terms and those discussed above are intended to encompass different orientations of the device in addition to the orientation depicted in the Figures.

The terminology used herein is for the purpose of describing particular embodiments only and is not intended to be limiting of the disclosure. As used herein, the singular forms "a," "an," and "the" are intended to include the plural forms as well, unless the context clearly indicates otherwise. It will be further understood that the terms "comprises," "comprising," "includes," and/or "including" when used herein specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this disclosure belongs. It will be further understood that terms used herein should be interpreted as having a meaning that is consistent with their meaning in the context of this specification and the relevant art and will not be interpreted in an idealized or overly formal sense unless expressly so defined herein.

Rapid assessment of microcirculation in tissue to realize closed-loop systems is provided. Microcirculatory assessment systems according to embodiments described herein allow a user to assess changes in local blood flow in microvasculature in real-time using conventional electrical techniques. The approach described herein can be used to assess hemorrhage during surgery, monitor progress and restoration after injury, monitor neuronal responses to stimulation of specific brain regions, etc. Some embodiments provide a closed-loop system that allows controlled administration of a therapeutic intervention to be delivered depending on blood flow changes being fed back to a controller. For example, calibrated doses of electrical stimulation can be delivered in a deep brain stimulation (DBS) system.

The approach described here is readily translatable with very minimal changes to existing hardware. Such closed-loop systems will improve the accuracy of therapeutic interventions, such as to improve electrode placement in DBS surgery and potentially reduce surgery time, optimize the delivery of therapeutic dosage (e.g., a dosage of electrical stimulation), increase battery life of implantable medical devices (e.g., DBS systems), reduce post-surgical visits to medical practitioners, and improve the quality of life of patients.

I. Introduction

As described above, blood flow in the microvasculature is indicative of a variety of clinically important biomarkers, such as presence of local hemorrhage, progression and restoration of injury, neuronal activity, etc. For example, DBS has been shown to cause blood flow changes in different brain regions consistently indicating the activation of a wide range of brain circuits. However, assessing blood flow during therapeutic interventions (such as DBS) using traditional approaches, such as magnetic resonance (MR)-based methods, is very challenging.

Embodiments described herein can assess and/or monitor real-time blood flow changes in various applications. For example, some embodiments assess local blood flow changes (e.g., blood flow changes within a vicinity of a sensor, such as within 1 millimeter (mm)) in tissues of ipsilateral cortical brain structures in both acute and chronic experiments in response to DBS. Further embodiments use a real-time technique to monitor changes in local blood flow that can be readily translated to clinical indicia, such as DBS responses.

An evaluation of these approaches was performed on adult rodents, wherein the sub-thalamic nuclei (STN) was stimulated using 0.3 microamperes (µA), 130 hertz (Hz) and 90 microsecond (µs) biphasic pulses. Blood flow was measured at the ipsilateral somatosensory and motor cortex using a laser Doppler flowmeter. In addition, electrochemical impedance was assessed in the above two areas continuously. At the end of the experiment, a lesioning current was used to confirm the location of stimulation electrodes.

Marginal but distinct changes in local blood flow were consistently observed in these evaluations, both in somatosensory and motor cortical regions, in response to DBS. Changes in electrochemical impedance were correlated to blood flow changes consistently. Accordingly, this disclosure concludes that electrochemical impedance can be used to monitor local blood flow changes (e.g., in the ipsilateral somatosensory and motor cortical neurons) in response to therapeutic interventions (e.g., DBS). Further embodiments described herein adapt this approach to measuring blood flow in other tissues and systems.

An exemplary embodiment addresses two very specific and important challenges that hinder DBS therapy in patients (e.g., human Parkinsonian patients):

1. Accurate placement of a stimulation electrode. The trajectory and location of the site of stimulation (e.g., STN) is mapped accurately using pre-surgical CT and MR imaging. The target location of the stimulation electrode can be only a few millimeters in each of the three dimensions. The locations of the electrodes are currently verified by using micro-electrode recordings of the neurons in the location of the stimulation electrodes. However, these recordings can be influenced by anesthesia and other sedatives used during surgery. In addition, a post-surgical CT can be used to confirm the location of electrode. However, errors in positioning of DBS electrodes are considered one of the main failure modes that result in decreased efficacy in mitigating tremors in Parkinsonian patients, and in some cases causes off-target cognitive deficits.

2. Assessing and maintaining efficacy of chronic stimulation. Current DBS therapy systems are open-loop, where periodic adjustment by an experienced neurologist is necessary to maintain the efficacy of the therapy. This can be a trial-and-error process, where repeated adjustment may be needed with limited guidance for improving efficacy.

Embodiments of the present disclosure use the discovery that blood flow changes in microvasculature can be monitored using an electrochemical impedance spectrogram (EIS) over a broad range of frequencies (0-10 KHz) of microelectrodes or implants with micro-scale electrodes on their surface. It is further found that the sensitivity of electrochemical impedances increases monotonically with decreasing frequencies of excitation voltages.

Embodiments described herein require minimal additional instrumentation beyond what is now currently used in the clinic and are therefore readily translatable to existing DBS systems (such as those developed by Medtronic and other manufacturers). In addition, these embodiments address the above-outlined challenges as follows:

1. Accurate placement of a stimulation electrode. In a first aspect, embodiments provide a real-time assessment of blood flow changes in cortical or other appropriate regions of the brain (which show consistent blood flow changes from DBS). In response to DBS of the STN, embodiments provide a microcirculatory assessment system that can be used to rapidly verify positioning of the stimulation electrode and therefore reduce surgery time and patient discomfort. More importantly, these embodiments reduce errors in placement of the stimulation electrode.

2. Assessing and maintaining efficacy of chronic stimulation. Further embodiments provide continuous feedback of blood flow responses from appropriate regions of the brain. This feedback provides for closed-loop DBS systems that will automatically adjust the dose of electrical stimulation based on blood flow responses to applied stimulation. This saves energy consumption (e.g., battery-life) of the implant by optimizing the stimulation dose, reduces visits to medical practitioners (e.g., neurologists), and improves quality of life of a patient.

The disclosure is described further below in two parts. First, Section II describes a microcirculatory assessment system which monitors and assesses changes in blood flow in the microvasculature in the brain using the EIS. Second, Section III describes a closed-loop DBS system using the microcirculatory assessment system. The blood flow changes captured in real-time by EIS measurements can be used as a feedback variable to adjust the dose of stimulation in the stimulation electrode using a simple proportional-integral-derivative (PID) control or other conventional control schemes or adaptive control schemes (if patient physiology is expected to change with time). Finally, Section IV describes a flow diagram of methods and Section V describes a computer system according to embodiments described herein.

II. Microcirculatory Assessment System

Figure 1:
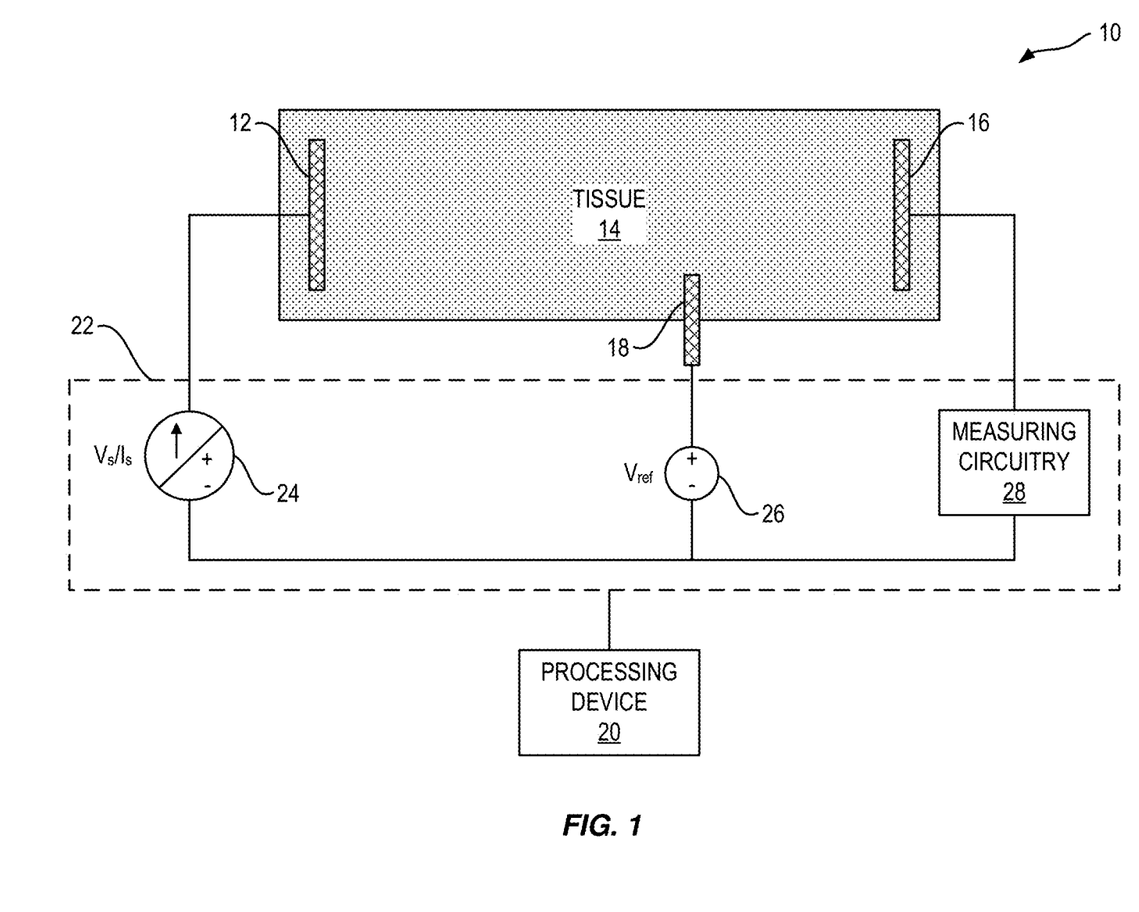
FIG. 1 is a block schematic diagram of a microcirculatory assessment system according to embodiments described herein.

FIG. 1 is a block schematic diagram of a microcirculatory assessment system 10 according to embodiments described herein. The microcirculatory assessment system 10 can include a 2-electrode or 3-electrode sensor design. In this regard, the microcirculatory assessment system 10 includes a working electrode 12 which provides a multi-frequency excitation signal (e.g., a triangular excitation signal) to tissue 14 (e.g., a region of tissue of a human or other animal patient, such as a region of the brain). The microcirculatory assessment system 10 further includes a counter electrode 16 which is used to measure an electrical parameter in response to the multi-frequency excitation signal.

In a first example, the multi-frequency excitation signal provided by the working electrode 12 is a voltage signal (v(t)), and the electrical parameter measured at the counter electrode 16 is a current response (i(t)). In a second example, the multi-frequency excitation signal provided by the working electrode 12 is a current signal (i(t)), and the electrical parameter measured at the counter electrode 16 is a voltage response (v(t)). In a 3-electrode sensor design, the microcirculatory assessment system 10 further includes a reference electrode 18 which provides a reference voltage (e.g., a ground or other reference level, Vref) for the working electrode 12 and/or the counter electrode 16. In a 2-electrode sensor design, the counter electrode 16 is instead configured to provide a reference voltage.

The tissue 14 represents a portion of a human or other animal body at which EIS measurements are gathered. For example, the tissue 14 can be a (portion of) a blood vessel, an organ (or tissue in an organ), a fluid (e.g., blood), etc. The working electrode 12 can be in contact with the tissue 14 at an appropriate position (e.g., within or on a surface of the tissue 14). The counter electrode 16 can be in contact with the tissue 14 at another position (e.g., away from the working electrode 12 and within or on the surface of the tissue 14). In some embodiments, the reference electrode 18 is positioned between the working electrode 12 and the counter electrode 16, and in other embodiments the reference electrode 18 is positioned adjacent to or away from the working electrode 12 or the counter electrode 16.

The microcirculatory assessment system 10 further includes a processing device 20 which obtains an EIS of the tissue 14. The EIS produced by the processing device 20 can be a sampled spectrogram based on the multi-frequency excitation signal and the measured electrical parameter. The EIS can be obtained using an approach described in concurrently filed U.S. patent application Ser. No. 17/196,324 filed on Mar. 9, 2021 (subsequently published as U.S. Patent Application Publication No. 2021/0278450 A1), entitled "Systems and Methods to Determine Electrochemical Impedance Spectrogram Rapidly in Real Time." Embodiments described herein use this method to rapidly assess EIS over a broad range of frequencies depending on the requirements of the given application. For the microcirculatory assessment system 10, a variety of broad-band signals can be used as the multi-frequency excitation signal, such as triangular waveforms (e.g., sawtooth waveforms, ramp waveforms), Chirp signals, etc., to rapidly assess EIS. Rapid assessment of blood flow (perfusion) in the microvasculature using EIS can be used in a variety of surgical and neurosurgical applications.

The processing device 20 can include or be coupled to additional circuitry 22, such as an excitation source 24, a reference source 26, and measuring circuitry 28. For example, where the multi-frequency excitation signal is a voltage signal, the measuring circuitry 28 can measure the response current (e.g., using a voltage divider or other circuitry) through the counter electrode 16 and provide an indication (e.g., a voltage signal representative of the response current) to the processing device 20. In other examples, measurements may be performed directly by the processing device 20.

The processing device 20 represents one or more commercially available or proprietary general-purpose processing devices, such as a microprocessor, central processing unit (CPU), or the like. The processing device 20 may be a microprocessor, field programmable gate array (FPGA), a digital signal processor (DSP), an application-specific integrated circuit (ASIC), or other programmable logic device, a discrete gate or transistor logic, discrete hardware components, or any combination thereof designed to perform the functions described herein. Furthermore, the processing device 20 may be a microprocessor, or may be any conventional processor, controller, microcontroller, or state machine. The processing device 20 may also be implemented as a combination of computing devices (e.g., a combination of a DSP and a microprocessor, a plurality of microprocessors, one or more microprocessors in conjunction with a DSP core, or any other such configuration).

The processing device 20 can cause the multi-frequency excitation signal to be generated in an appropriate manner. For example, a triangular excitation signal is readily generated in current conventional electrochemical workstations using a cyclic-voltammogram feature. In embedded systems (e.g., the therapeutic intervention system described in Section III), the processing device 20 includes or is connected to the excitation source 24, which can provide the multi-frequency excitation signal (e.g., a triangular excitation signal) having a desired shape, period (e.g., resolution) and amplitude (e.g., according to material properties of the tissue 14). In further examples, the excitation source 24 may be programmable to provide multi-frequency excitation signals with different shapes (e.g., a ramp signal, a sawtooth signal, a combination signal), different periods (e.g., a constant or varying period), and different amplitudes (e.g., an amplitude which is constant over periods or varying across periods).

In an exemplary aspect, the processing device 20 causes the working electrode 12 to generate the multi-frequency excitation signal (v(t) or i(t)) and obtains an electrical parameter measurement (i(t) or v(t)) at the counter electrode 16 in response to the multi-frequency excitation signal. The processing device 20 further obtains a Fourier transform of the multi-frequency excitation signal (e.g., by performing a fast Fourier transform (FFT) or retrieving a stored Fourier transform from memory) and a Fourier transform (e.g., FFT) of the measured electrical parameter. In this manner, the processing device 20 obtains a voltage spectrogram V(w) and a current spectrogram I(w), and uses a ratio of V(w) to I(w) to obtain a corresponding impedance spectrogram Z(w). From the impedance spectrogram Z(w), the processing device 20 determines the EIS, as described further below.

In some embodiments, the processing device 20 includes or is coupled to a memory storing one or more measurement profiles. The measurement profile(s) may include excitation signal parameters (e.g., whether a voltage or current waveform is to be generated, a shape, an amplitude, a period), a Fourier transform of the excitation signal, an expected range of response signal, and so on. The measurement profile(s) may improve performance of the microcirculatory assessment system 10 and/or provide flexibility to measure multiple types of tissues 14.

A. Example Multi-Frequency Excitation Signals

Figure 2A:
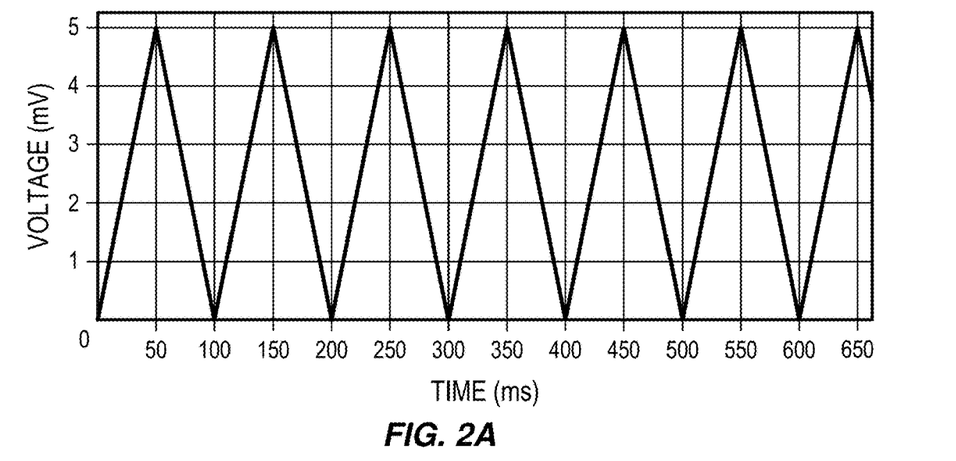
FIG. 2A is a graphical representation of a ramp excitation voltage signal with an amplitude of 5 millivolts (mV) at 100 mV per second (mV/s).
Figure 2B:
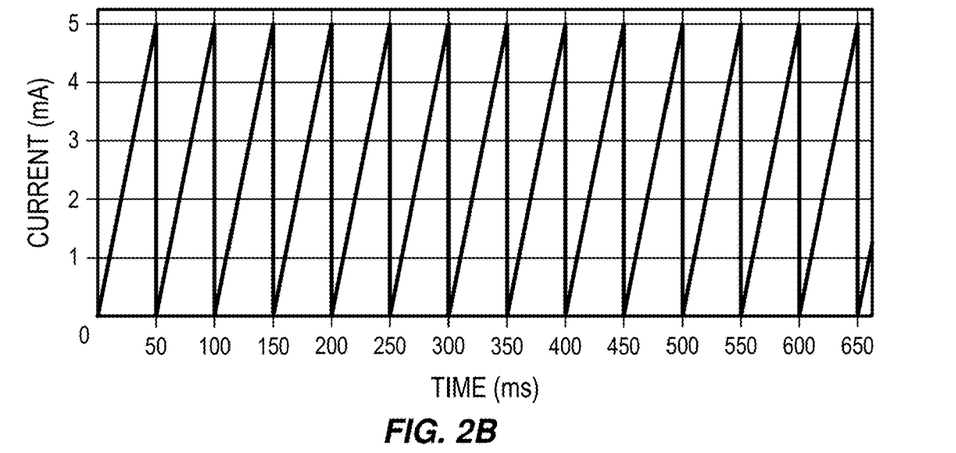
FIG. 2B is a graphical representation of a sawtooth excitation current signal with an amplitude of 5 milliamperes (mA) at 100 mV/s.
Figure 2C:
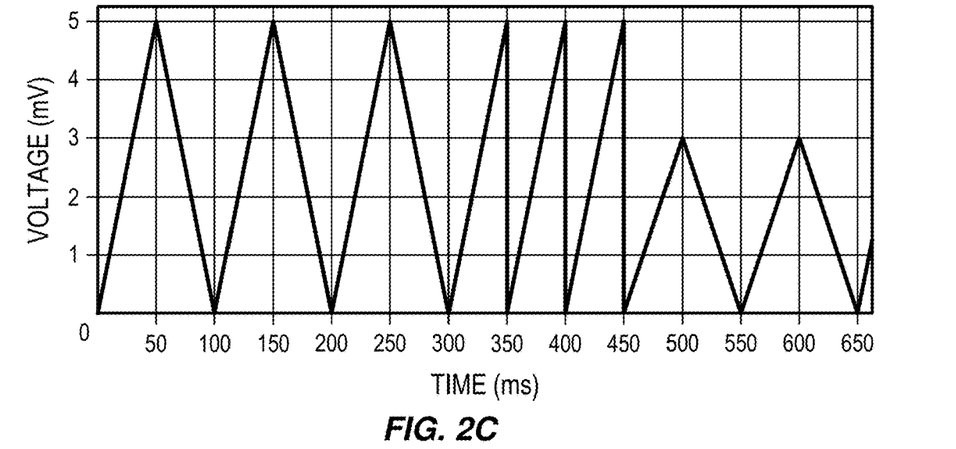
FIG. 2C is a graphical representation of a mixed ramp and sawtooth excitation voltage signal with a varying amplitude.

FIGS. 2A-2C illustrate various examples of excitation signals which may be generated by the microcirculatory assessment system 10 of FIG. 1. For example, FIG. 2A is a graphical representation of a ramp excitation voltage signal with an amplitude of 5 millivolts (mV) at 100 mV per second (mV/s). As demonstrated further below, this excitation voltage signal results in a current response. Because the ramp excitation voltage signal has a period of 100 milliseconds (ms), it results in an EIS resolution of 10 Hz.

FIG. 2B is a graphical representation of a sawtooth excitation current signal with an amplitude of 5 milliamperes (mA) at 100 mV/s. This excitation current signal results in a voltage response. Because the sawtooth excitation current signal has a period of 50 ms, it results in an EIS resolution of 20 Hz.

FIG. 2C is a graphical representation of a mixed ramp and sawtooth excitation voltage signal with a varying amplitude. In addition to uniform signals (e.g., as in FIGS. 2A and 2B), some embodiments may use mixed signals having multiple waveform shapes, amplitudes, and/or periods (e.g., for different applications, such as a different material or to measure particular types of responses).

B. Example EIS Measurements

Figure 3A:
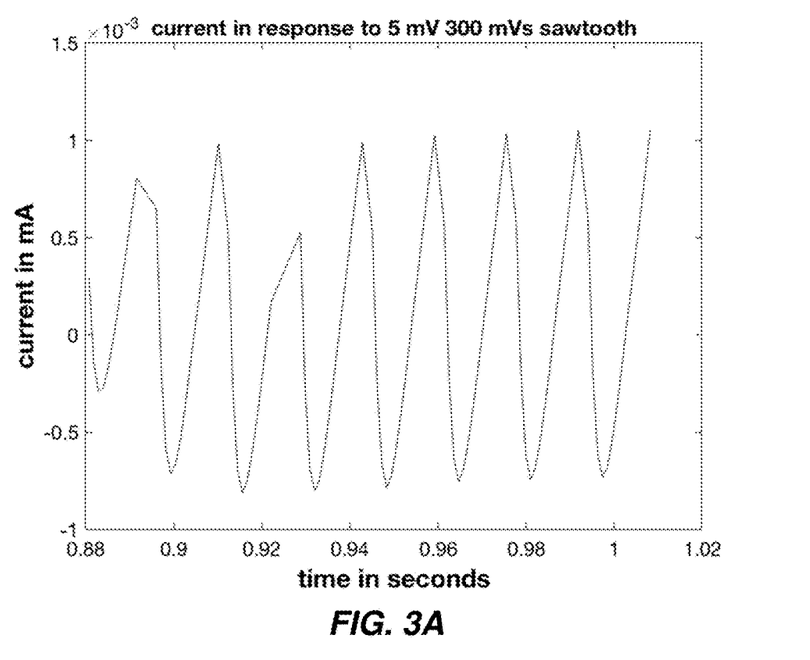
FIG. 3A is a graphical representation of current measurements in response to a 5 mV, 300 mV/s sawtooth excitation voltage signal.
Figure 3B:
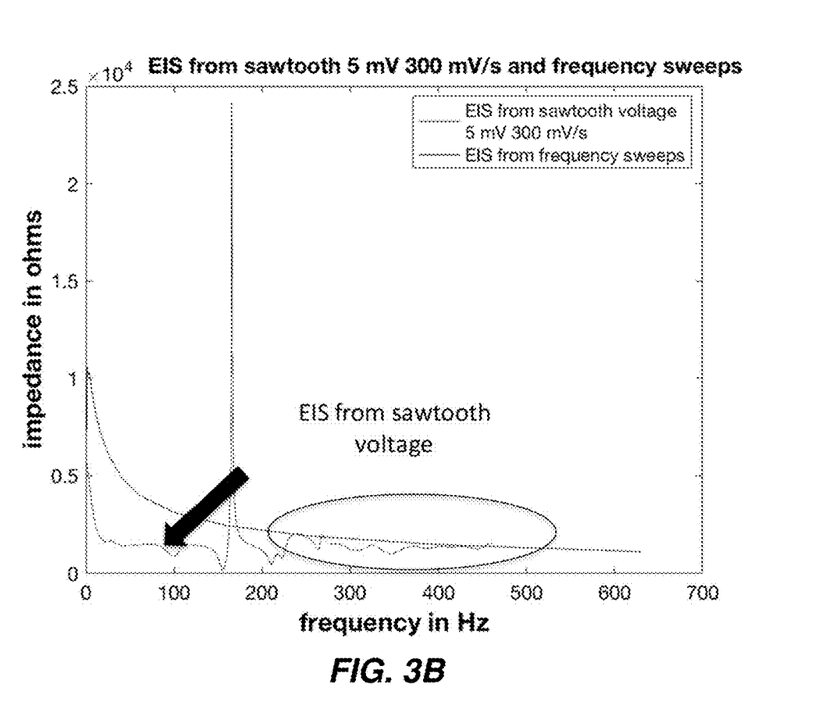
FIG. 3B is a graphical representation of a measured electrochemical impedance spectrogram (EIS) in response to the sawtooth excitation voltage signal and current measurements of FIG. 3A.

FIG. 3A is a graphical representation of current measurements in response to a 5 mV, 300 mV/s sawtooth excitation voltage signal. FIG. 3B is a graphical representation of a measured EIS in response to the sawtooth excitation voltage signal and current measurements of FIG. 3A. The smooth curve represents the EIS from a traditional frequency sweep. The encircled region shows good agreement between the EIS obtained from the traditional frequency sweep (over several minutes) and the EIS obtained from sawtooth voltages (over a minimum of 0.02 seconds to 1 second).

In the example of FIGS. 3A and 3B, a major discrepancy is seen in the EIS at low frequencies. Any spikes are due to noise from resolution issues in the FFT. The EIS from sawtooth is also wavy with values at the crests being more reliable due to high signal-to-noise ratio (SNR). In an exemplary aspect, the processing device 20 of FIG. 1 is configured to produce a sampled EIS using the peak values (e.g., values at harmonics of the fundamental frequency of the excitation signal) within a range that is considered reliable for the given material and excitation signal. For example, a measurement profile may be associated with the type of the tissue being measured, and the measurement profile may include a frequency range where the EIS is considered accurate (e.g., in addition to excitation signal parameters, a Fourier transform of the excitation signal, an expected range of response signal, etc.).

C. Example Blood Flow Measurements

Figure 4A:
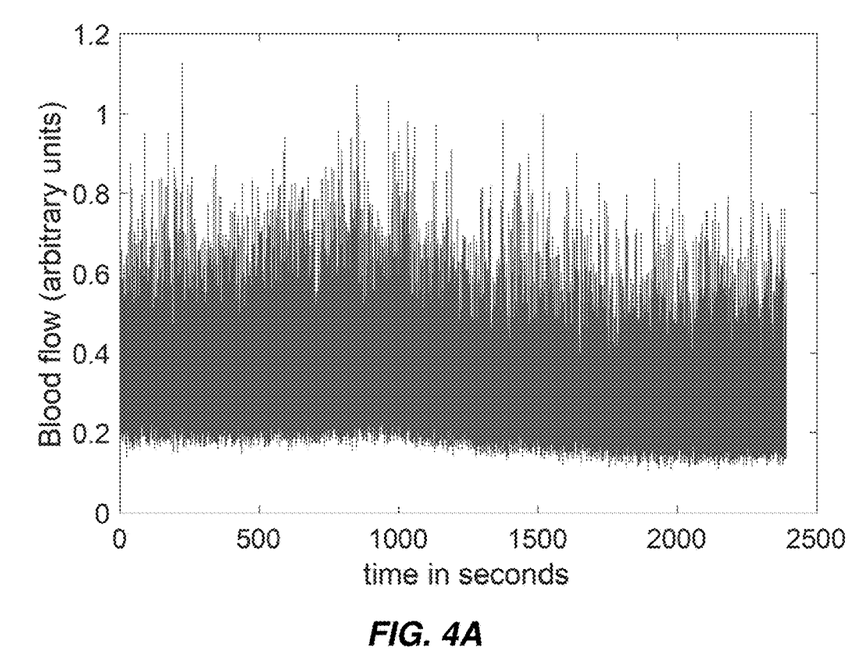
FIG. 4A is a graphical representation of local blood flow of a patient over time.

FIG. 4A is a graphical representation of local blood flow of a patient over time. This graph just depicts baseline blood flow and blood flow after a first administration of endothelin (ET1)—a vasoconstrictor. A second higher dose of endothelin was administered, which caused the blood flow to reduce even more.

Figure 4B:
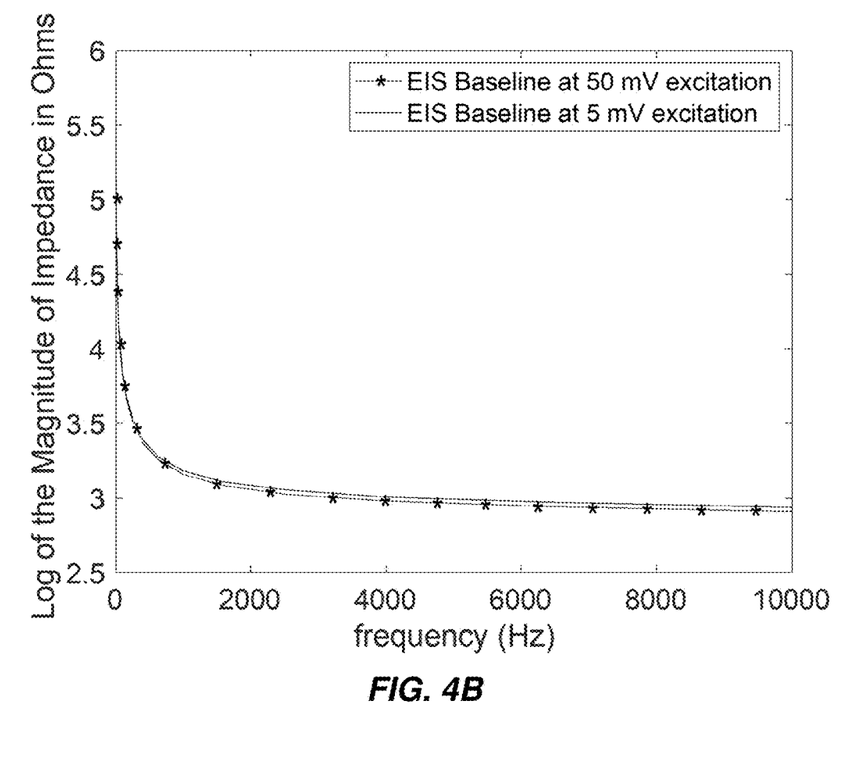
FIG. 4B is a graphical representation of a logarithmic scale of a measured EIS.

FIG. 4B is a graphical representation of a logarithmic scale of a measured EIS. The EIS is measured at 5 mV and 50 mV to assess if there is any impact on impedance values after changing the amplitude of the test signal. As can be seen, there was no significant difference between the two measurements. Some embodiments of the microcirculatory assessment system 10 use a 50 mV excitation signal because it yields cleaner data for the blood flow assessment (i.e., a larger signal produces a higher and more measurable current). Other embodiments may use a lower voltage signal (e.g., to reduce energy consumption).

III. Closed-Loop Therapeutic Intervention System

Figure 5:
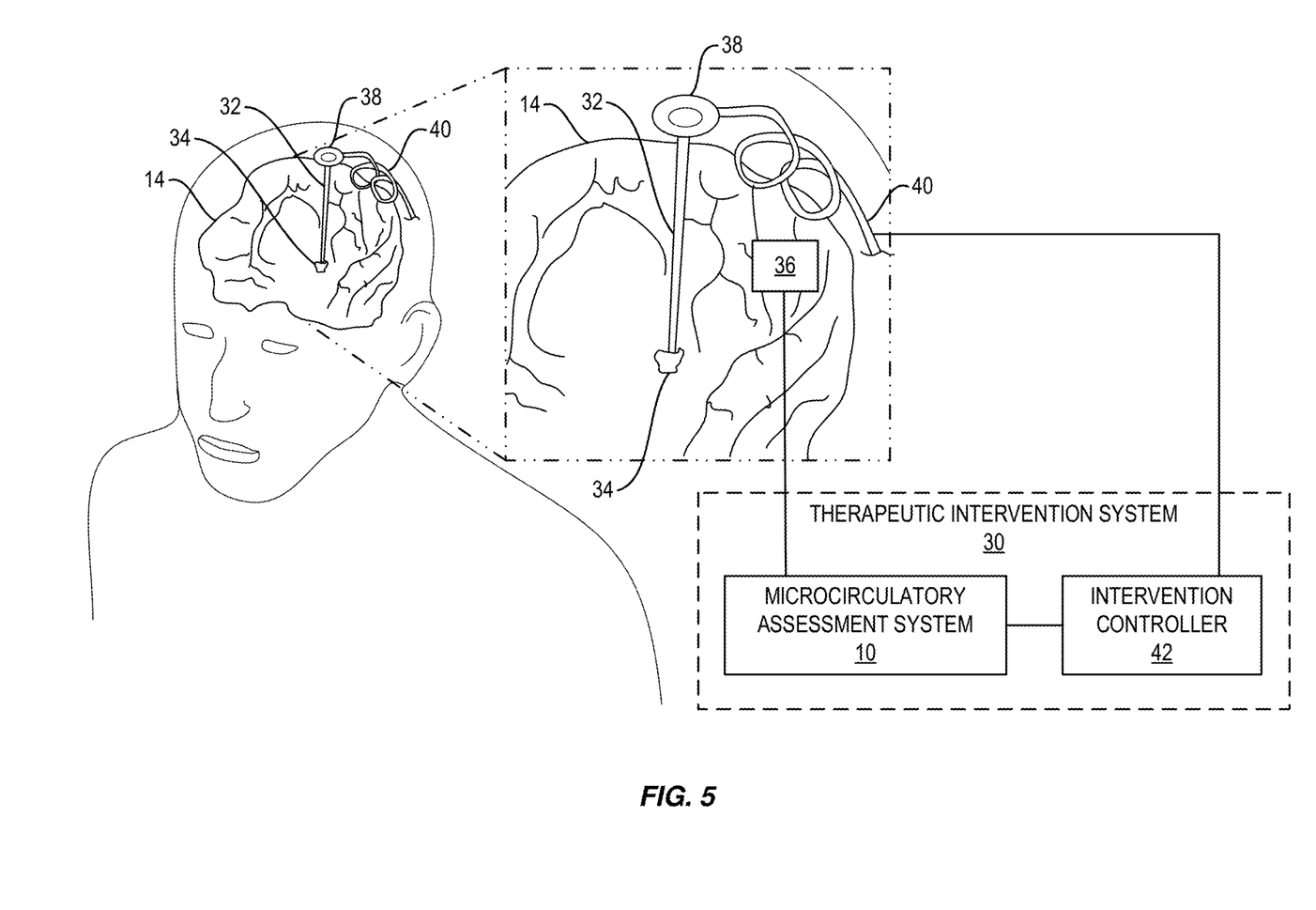
FIG. 5 is a schematic diagram of a closed-loop therapeutic intervention system 30 using the microcirculatory assessment system of FIG. 1 according to embodiments described herein.

FIG. 5 is a schematic diagram of a closed-loop therapeutic intervention system 30 using the microcirculatory assessment system 10 of FIG. 1 according to embodiments described herein. The closed-loop therapeutic intervention system 30 can be implemented as an adaptation of traditional therapeutic intervention systems with the addition of the microcirculatory assessment system 10, or it can be implemented as an independent solution. Example applications of the therapeutic intervention system 30 include, but are not limited to, bioelectronic intervention (e.g., a DBS system or other neurological stimulatory system), biochemical intervention (e.g., providing a chemical stimulation), administration of a pharmaceutical, and administration of other stimuli (e.g., electrical, ultrasound, optical, magnetic, etc.).

In an exemplary aspect, the illustrated therapeutic intervention system 30 is a DBS system. The therapeutic intervention system 30 includes a stimulation electrode 32 (or other therapeutic intervention apparatus), which is in contact with a region of the tissue 14 (e.g., a STN 34 or another tissue being stimulated). The stimulation electrode 32 provides an electrical stimulation to that region of the tissue 14 (e.g., as a therapeutic for Parkinson's disease or another medical condition). EIS electrodes 36 (e.g., the working electrode 12, counter electrode 16, and/or reference electrode 18 of FIG. 1) are placed in contact with another region of the tissue 14 (e.g., ipsilateral cortical brain structures) or another tissue to measure a local blood flow response to the electrical stimulation from the stimulation electrode 32.

The stimulation electrode 32 is connected to the therapeutic intervention system 30 through a lead 38 and/or lead wires 40. An intervention controller 42 controls operation of the therapeutic intervention system 30, including controlling the electrical stimulation (or other therapeutic intervention) provided by the stimulation electrode 32 (or other therapeutic intervention apparatus). The intervention controller 42 can include or be coupled to the processing device 20 of the microcirculatory assessment system 10 of FIG. 1. Similar to the processing device 20, the intervention controller 42 may be a microprocessor, CPU, FPGA, DSP, ASIC, or other programmable logic device, a discrete gate or transistor logic, discrete hardware components, or any combination thereof designed to perform the functions described herein. Furthermore, the processing device 20 may be a microprocessor, or may be any conventional processor, controller, microcontroller, or state machine. The processing device 20 may also be implemented as a combination of computing devices (e.g., a combination of a DSP and a microprocessor, a plurality of microprocessors, one or more microprocessors in conjunction with a DSP core, or any other such configuration).

In an exemplary aspect, the intervention controller 42 cooperates with the microcirculatory assessment system 10 to monitor blood flow in the tissue 14 in response to the electrical stimulation provided by the stimulation electrode 32. In this manner, the results of monitoring the blood flow in the tissue 14 can be used to adjust placement of the stimulation electrode 32, provide feedback to a user (e.g., using a monitor, audio device, or other output device), and/or adjust a dose of the electrical stimulation (or other therapeutic intervention) provided by the stimulation electrode 32. In some examples, adjusting the dose of an intervention uses an automatic control in response to the measured blood flow or EIS. In other examples, such adjustments may be semi-automatic, such as by providing feedback to a user (e.g., a medical practitioner or patient), receiving an input from the user (e.g., via an input device such as a button, keyboard, mouse, camera, audio input device, etc.), and adjusting the dose of the intervention in response to the user input.

The blood flow changes captured in real-time by EIS measurements with the microcirculatory assessment system 10 can be used as a feedback variable to adjust the dose of stimulation in the stimulation electrode 32. For example, the intervention controller 42 can automatically adjust the therapeutic intervention using a proportional-integral-derivative (PID) control or other control schemes. In other examples, an adaptive control scheme can be used where patient physiology is expected to change with time.

A. Example Blood Flow Response Measurements

Figure 6A:
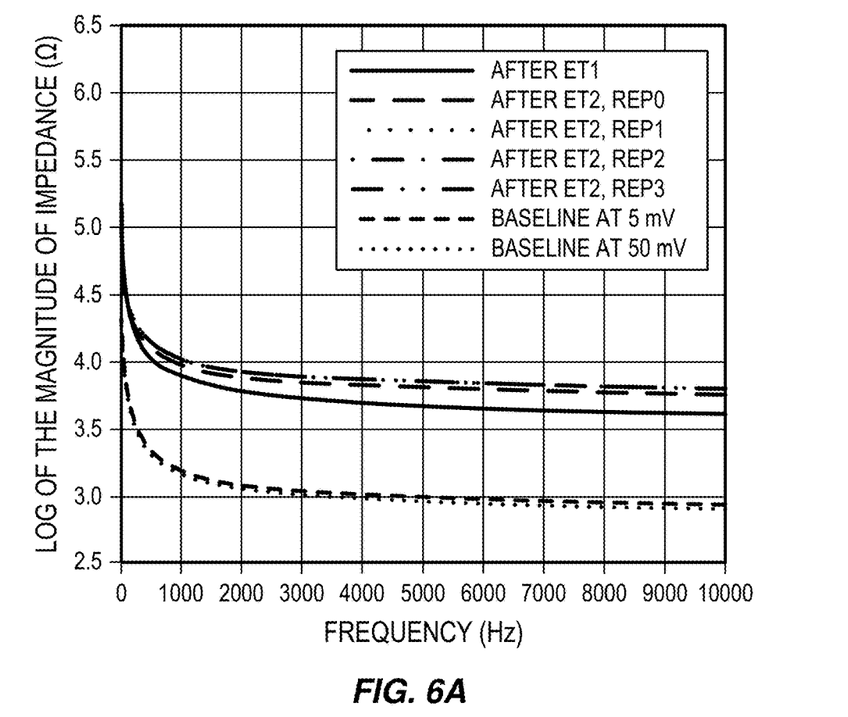
FIG. 6A is a graphical representation of a logarithmic scale of a measured EIS with administrations of endothelin.

FIG. 6A is a graphical representation of a logarithmic scale of a measured EIS with administrations of endothelin. The EIS changes (increases) with decreasing blood flow (caused by the first and second administration of endothelin, labeled ET1 and ET2 in the legend, respectively).

Figure 6B:
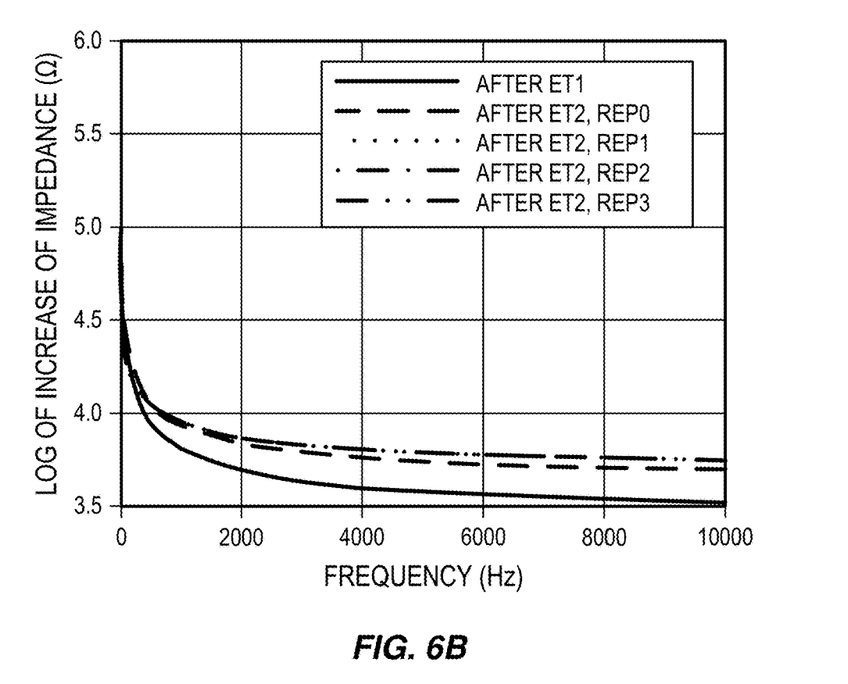
FIG. 6B is a graphical representation of the increase in impedance over the baseline.

FIG. 6B is a graphical representation of the increase in impedance over the baseline. In other words, this is the difference graph of FIG. 6A.

Figure 7A:
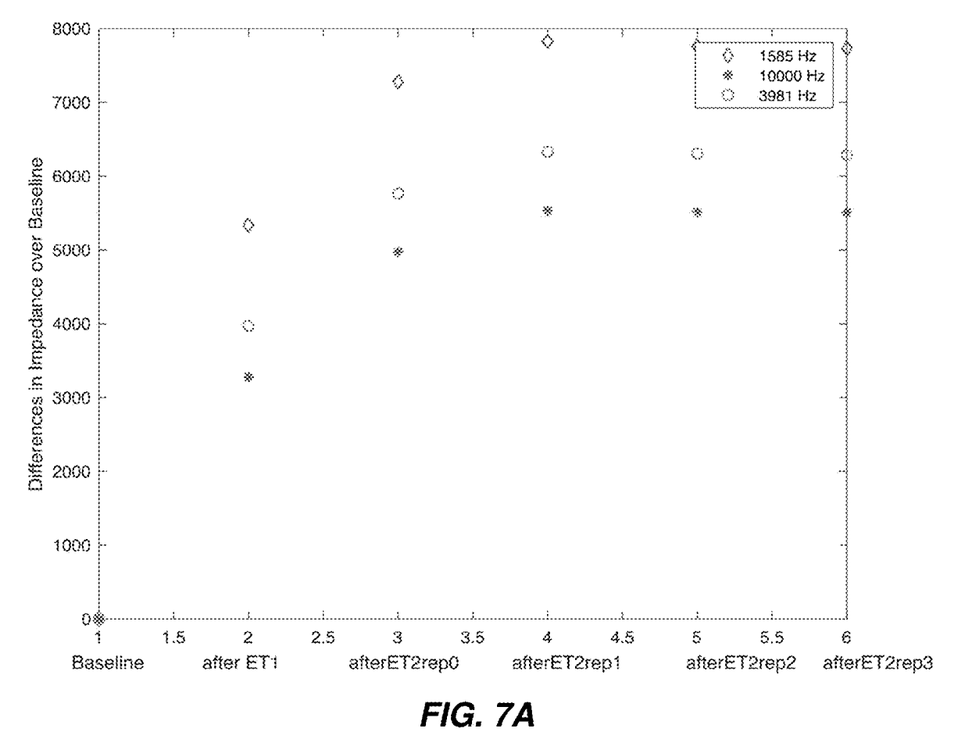
FIG. 7A is a graphical representation of increase in impedance (over baseline) at 3 different frequencies as a function of blood flow.

FIG. 7A is a graphical representation of increase in impedance (over baseline) at 3 different frequencies as a function of blood flow.

Figure 7B:
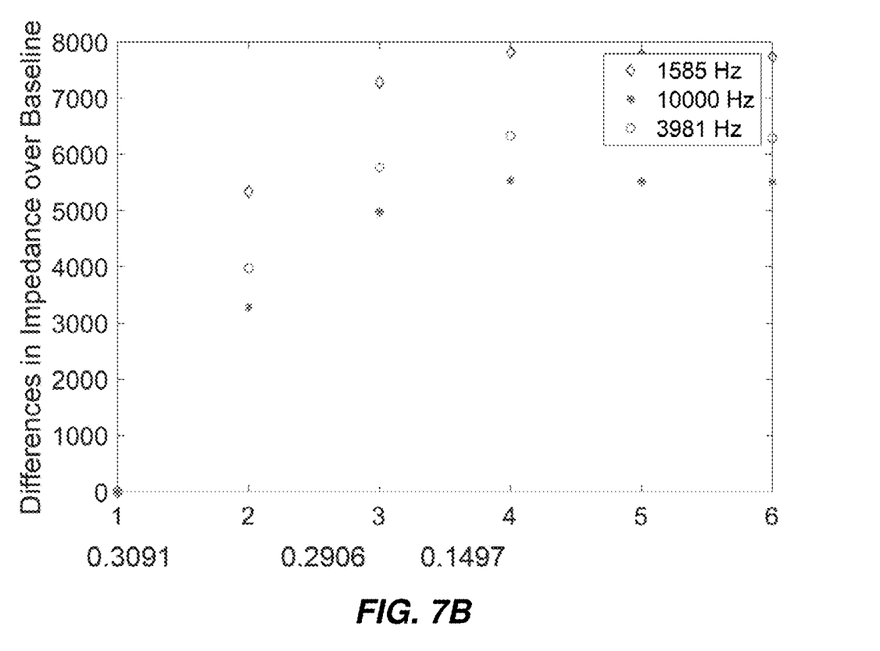
FIG. 7B is a graphical representation of average blood flow numbers at 3 different time-instants.

FIG. 7B is a graphical representation of average blood flow numbers at 3 different time-instants. For instance, the index 1 corresponds to a baseline flow of 0.3091 (arbitrary perfusion units), flow after a second administration of ET1 is 0.1497 (arbitrary perfusion units) between indices 3 and 4, along the x-axis.

IV. Flow Diagram

Figure 8:
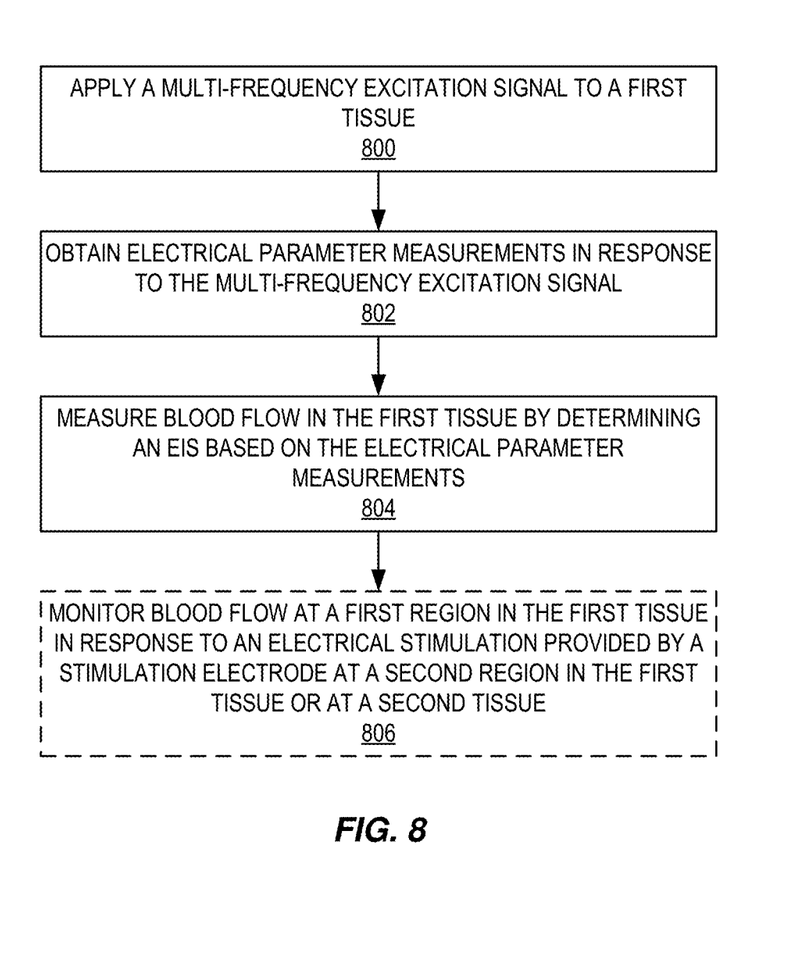
FIG. 8 is a flow diagram illustrating a process for measuring blood flow.

FIG. 8 is a flow diagram illustrating a process for measuring blood flow. Dashed boxes represent optional steps. The process begins at operation 800, with applying a multi-frequency excitation signal to a first tissue (e.g., the tissue 14 of FIG. 1). In an exemplary aspect, the multi-frequency excitation signal is a triangular voltage signal (or a current signal) with a sawtooth or ramp waveform. The process continues at operation 802, with obtaining electrical parameter measurements in response to the multi-frequency excitation signal. In an exemplary aspect, the electrical parameter measurements are current measurements (or voltage measurements).

The process continues at operation 804, with measuring blood flow in the first tissue by determining an EIS based on the electrical parameter measurements. Measuring the EIS of the first tissue can include determining a ratio of Fourier transforms (e.g., FFTs) of voltages of the triangular excitation signal and corresponding current measurements. Changes in the blood flow can be measured as proportional to changes in the EIS. The process optionally continues at operation 806, with monitoring blood flow at a first region in the first tissue in response to an electrical stimulation provided by a stimulation electrode at a second region in the first tissue or at a second tissue.

Figure 9:
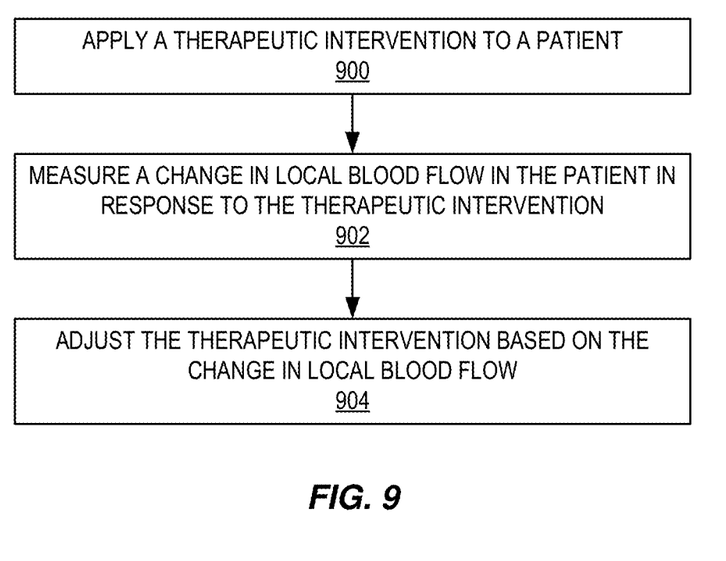
FIG. 9 is a flow diagram illustrating a process for providing a controlled therapeutic intervention.

FIG. 9 is a flow diagram illustrating a process for providing a controlled therapeutic intervention. Dashed boxes represent optional steps. The process begins at operation 900, with applying a therapeutic intervention to a patient (e.g., a tissue of a patient). The process continues at operation 902, with measuring a change in local blood flow in the patient in response to the therapeutic intervention. In an exemplary aspect, the local blood flow is measured as a change in an EIS at a tissue of the patient (e.g., the same or another tissue of the patient). The process continues at operation 904, with adjusting the therapeutic intervention based on the change in local blood flow. Adjusting the therapeutic intervention can be performed automatically or with some input from a user (e.g., by providing feedback to the user and receiving a user input).

Although the operations of FIGS. 8 and 9 are illustrated in a series, this is for illustrative purposes and the operations are not necessarily order dependent. Some operations may be performed in a different order than that presented. Further, processes within the scope of this disclosure may include fewer or more steps than those illustrated in FIGS. 8 and 9.

V. Computer System

Figure 10:
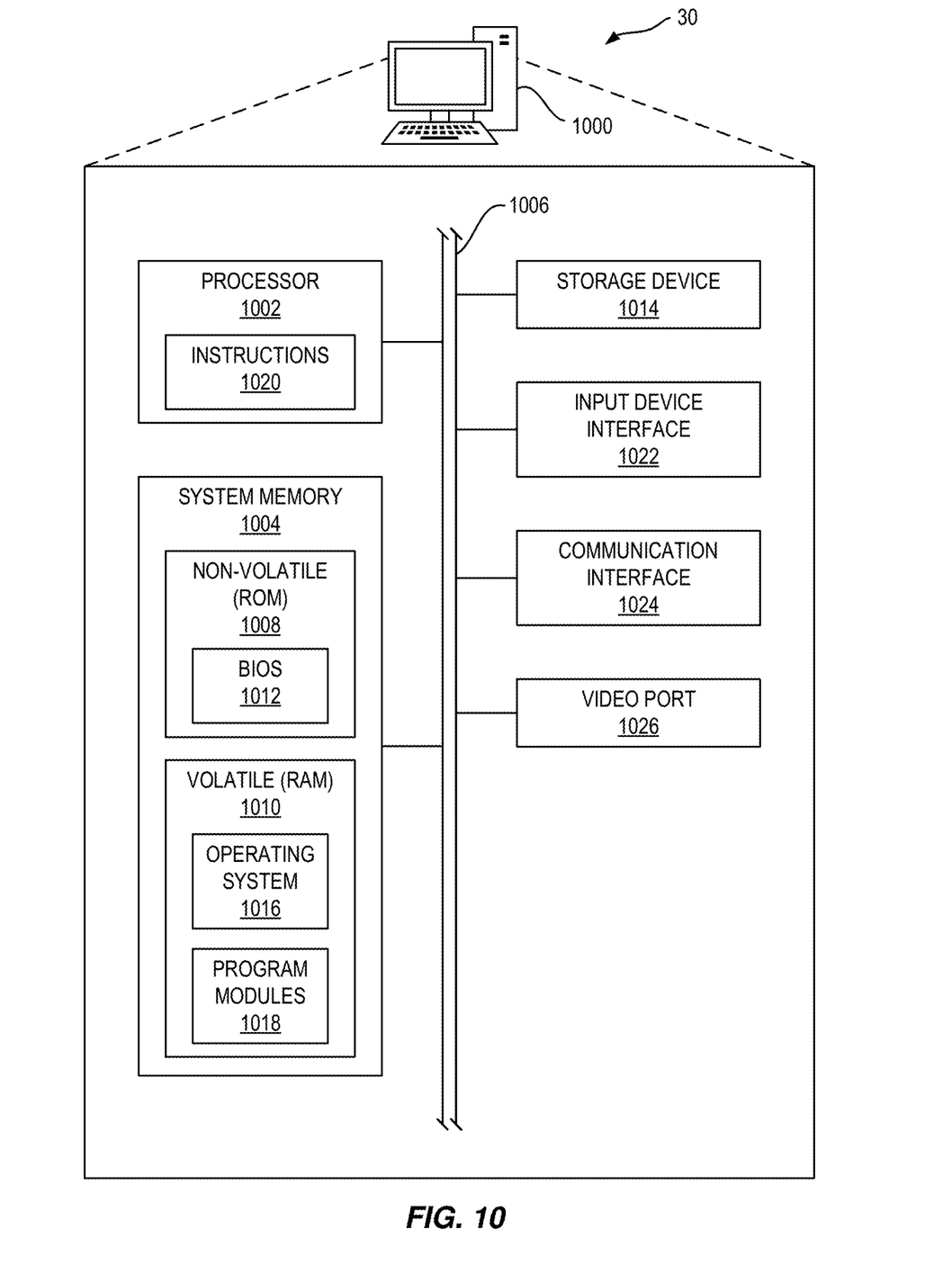
FIG. 10 is a block diagram of a therapeutic intervention system suitable for implementing the method for providing a controlled therapeutic intervention according to embodiments disclosed herein.

FIG. 10 is a block diagram of a therapeutic intervention system 30 suitable for implementing the method for providing a controlled therapeutic intervention according to embodiments disclosed herein. The therapeutic intervention system 30 (which may include the microcirculatory assessment system 10 of FIG. 1) includes or is implemented as a computer system 1000, which comprises any computing or electronic device capable of including firmware, hardware, and/or executing software instructions that could be used to perform any of the methods or functions described above, such as measuring blood flow and providing feedback to control the therapeutic intervention system 30. In this regard, the computer system 1000 may be a circuit or circuits included in an electronic board card, such as a printed circuit board (PCB), a server, a personal computer, a desktop computer, a laptop computer, an array of computers, a personal digital assistant (PDA), a computing pad, a mobile device, or any other device, and may represent, for example, a server or a user's computer.

The exemplary computer system 1000 in this embodiment includes a processor 1002 (e.g., the processing device 20 of FIG. 1 and/or the intervention controller 42, which may be considered a single processor), a system memory 1004, and a system bus 1006. The system memory 1004 may include non-volatile memory 1008 and volatile memory 1010. The non-volatile memory 1008 may include read-only memory (ROM), erasable programmable read-only memory (EPROM), electrically erasable programmable read-only memory (EEPROM), and the like. The volatile memory 1010 generally includes random-access memory (RAM) (e.g., dynamic random access memory (DRAM), such as synchronous DRAM (SDRAM)). A basic input/output system (BIOS) 1012 may be stored in the non-volatile memory 1008 and can include the basic routines that help to transfer information between elements within the computer system 1000.

The system bus 1006 provides an interface for system components including, but not limited to, the system memory 1004 and the processing device 1002. The system bus 1006 may be any of several types of bus structures that may further interconnect to a memory bus (with or without a memory controller), a peripheral bus, and/or a local bus using any of a variety of commercially available bus architectures.

As described above, the processing device 1002 represents one or more commercially available or proprietary general-purpose processing devices, such as a microprocessor, CPU, or the like. More particularly, the processing device 1002 may be a complex instruction set computing (CISC) microprocessor, a reduced instruction set computing (RISC) microprocessor, a very long instruction word (VLIW) microprocessor, a processor implementing other instruction sets, or other processors implementing a combination of instruction sets. The processing device 1002 is configured to execute processing logic instructions for performing the operations and steps discussed herein. In this regard, the various illustrative logical blocks, modules, and circuits described in connection with the embodiments disclosed herein may be implemented or performed with the processing device 1002.

The computer system 1000 may further include or be coupled to a non-transitory computer-readable storage medium, such as a storage device 1014, which may represent an internal or external hard disk drive (HDD), flash memory, or the like. The storage device 1014 and other drives associated with computer-readable media and computer-usable media may provide non-volatile storage of data, data structures, computer-executable instructions, and the like. Although the description of computer-readable media above refers to an HDD, it should be appreciated that other types of media that are readable by a computer, such as optical disks, magnetic cassettes, flash memory cards, cartridges, and the like, may also be used in the operating environment, and, further, that any such media may contain computer-executable instructions for performing novel methods of the disclosed embodiments.

An operating system 1016 and any number of program modules 1018 or other applications can be stored in the volatile memory 1010, wherein the program modules 1018 represent a wide array of computer-executable instructions corresponding to programs, applications, functions, and the like that may implement the functionality described herein in whole or in part, such as through instructions 1020 on the processing device 1002. The program modules 1018 may also reside on the storage mechanism provided by the storage device 1014. As such, all or a portion of the functionality described herein may be implemented as a computer program product stored on a transitory or non-transitory computer-usable or computer-readable storage medium, such as the storage device 1014, non-volatile memory 1008, volatile memory 1010, instructions 1020, and the like. The computer program product includes complex programming instructions, such as complex computer-readable program code, to cause the processing device 1002 to carry out the steps necessary to implement the functions described herein.

An operator, such as the user, may also be able to enter one or more configuration commands to the computer system 1000 through a keyboard, a pointing device such as a mouse, or a touch-sensitive surface, such as the display device, via an input device interface 1022 or remotely through a web interface, terminal program, or the like via a communication interface 1024. The communication interface 1024 may be wired or wireless and facilitate communications with any number of devices via a communications network in a direct or indirect fashion. An output device, such as a display device, can be coupled to the system bus 1006 and driven by a video port 1026. Additional inputs and outputs to the computer system 1000 may be provided through the system bus 1006 as appropriate to implement embodiments described herein.

The operational steps described in any of the exemplary embodiments herein are described to provide examples and discussion. The operations described may be performed in numerous different sequences other than the illustrated sequences. Furthermore, operations described in a single operational step may actually be performed in a number of different steps. Additionally, one or more operational steps discussed in the exemplary embodiments may be combined.

Those skilled in the art will recognize improvements and modifications to the preferred embodiments of the present disclosure. All such improvements and modifications are considered within the scope of the concepts disclosed herein and the claims that follow.

What is claimed is:

1. A therapeutic intervention system, comprising:
an intervention controller configured to provide a controlled therapeutic intervention to a patient; and
a microcirculatory assessment system configured to measure a change in local blood flow in the patient in response to the controlled therapeutic intervention;
wherein the microcirculatory assessment system comprises: (i) a counter electrode configured to measure an electrical response to a multi-frequency excitation signal applied to a tissue of the patient, and (ii) a processing device coupled to the electrode and configured to perform the following items (a) and (b): (a) determine an electrochemical impedance spectrogram (EIS) from the electrical response to the multi-frequency excitation signal, and (b) measure blood flow of the tissue based on the EIS;
wherein the intervention controller is further configured to adjust the controlled therapeutic intervention based on the change in local blood flow.

2. A method for providing a controlled therapeutic intervention using the therapeutic intervention system of claim 1, the method comprising:
applying a controlled therapeutic intervention to a patient utilizing the intervention controller;
measuring a change in local blood flow in the patient, utilizing the microcirculatory assessment system, in response to the therapeutic intervention; and
adjusting the therapeutic intervention, utilizing the intervention controller, based on the change in local blood flow.

3. The method of claim 2, wherein measuring the change in local blood flow comprises measuring a change in an electrochemical impedance spectrogram (EIS) at a tissue of the patient.

4. The method of claim 3, wherein measuring the change in the EIS comprises:
applying a multi-frequency excitation signal to the tissue;
obtaining electrical parameter measurements in response to the multi-frequency excitation signal; and
measuring the EIS as a function of the electrical parameter measurements and the multi-frequency excitation signal.

5. The method of claim 4, wherein the multi-frequency excitation signal comprises a triangular excitation signal having at least one of a ramp waveform or a sawtooth waveform.

6. The method of claim 4, wherein determining the EIS comprises determining a ratio of a fast Fourier transform (FFT) of the multi-frequency excitation signal and a FFT of the electrical parameter measurements.

7. The method of claim 3, wherein measuring the change in local blood flow comprises determining changes in blood flow as proportional to changes in the EIS.

8. The method of claim 2, wherein the therapeutic intervention comprises a neurological stimulation.

9. The method of claim 8, wherein:
applying the therapeutic intervention comprises applying an electrical stimulation using a stimulation electrode at a first region of a first tissue of the patient; and
measuring the change in local blood flow comprises monitoring blood flow at a second region in the first tissue or a second tissue of the patient in response to the electrical stimulation.

10. The method of claim 9, wherein adjusting the therapeutic intervention comprises adjusting placement of the stimulation electrode based on results of monitoring the blood flow in response to the electrical stimulation.

11. The method of claim 9, wherein adjusting the therapeutic intervention comprises providing feedback to a user based on results of monitoring the blood flow in response to the electrical stimulation.

12. The method of claim 9, wherein adjusting the therapeutic intervention comprises adjusting a dose of the electrical stimulation provided by the stimulation electrode based on results of monitoring the blood flow in response to the electrical stimulation.

13. The method of claim 12, wherein the dose of the electrical stimulation is adjusted using an automatic control.

14. The method of claim 13, wherein the automatic control is a proportional-integral-derivative (PID) control.

15. The method of claim 13, wherein the automatic control comprises an adaptive control scheme.

16. The method of claim 2, wherein the therapeutic intervention comprises one or more of chemical stimulation, a bioelectronic intervention, administration of a pharmaceutical, an electrical stimulation, an ultrasound stimulation, an optical stimulation, or a magnetic stimulation.

17. The therapeutic intervention system of claim 1, wherein:
- the intervention controller is configured to provide an electrical stimulation in a first tissue of the patient using a stimulation electrode; and
- the microcirculatory assessment system is further configured to monitor blood flow in the first tissue or a second tissue in response to the electrical stimulation in the first tissue.

18. The therapeutic intervention system of claim 17, wherein the intervention controller is further configured to adjust a dose of the electrical stimulation provided by the stimulation electrode in response to changes in the monitored blood flow of the first tissue or the second tissue.

19. The therapeutic intervention system of claim 17, wherein the therapeutic intervention system comprises a closed-loop deep brain stimulation (DBS) system.

* * * * *